United States Patent [19]

Hill et al.

[11] Patent Number: 4,896,973
[45] Date of Patent: Jan. 30, 1990

[54] THERMOMECHANICAL ANALYSIS APPARATUS

[75] Inventors: Harold I. Hill, Fairfield; Michael J. O'Neill, Wilton; Thomas M. Murray, Trumbull, all of Conn.

[73] Assignee: The Perkin-Elmer Corporation, Norwalk, Conn.

[21] Appl. No.: 704,353

[22] Filed: Feb. 21, 1985

[51] Int. Cl.$^4$ .............................................. G01N 25/16
[52] U.S. Cl. ........................................... 374/56; 374/55
[58] Field of Search .................... 374/6, 7, 55, 56–57; 336/30, 136; 33/147 D, 148 D

[56] References Cited

U.S. PATENT DOCUMENTS

| | | | |
|---|---|---|---|
| 3,474,658 | 10/1969 | Levy et al. | 374/56 |
| 3,589,167 | 6/1971 | Hill | 374/56 |
| 3,680,357 | 8/1972 | Clusener | 336/136 |
| 4,019,365 | 4/1977 | Woo | 374/55 |
| 4,354,764 | 10/1982 | Achermann et al. | 374/56 |

FOREIGN PATENT DOCUMENTS 2331113  5/1975  Fed. Rep. of Germany .

Primary Examiner—William A. Cuchlinski, Jr.
Assistant Examiner—Thomas B. Will
Attorney, Agent, or Firm—Thomas P. Murphy; Edwin T. Grimes

[57] ABSTRACT

A thermomechanical analysis apparatus includes a probe assembly supported in substantially weightless contact with a sample material over a range of displacement of the probe by means of a linear motor controlled from a constant current source. The probe assembly is automatically weighed by measuring and storing the value of the current needed to raise the probe, that value is thereafter employed during the analysis mode to maintain the probe assembly in a substantially weightless condition.

9 Claims, 3 Drawing Sheets

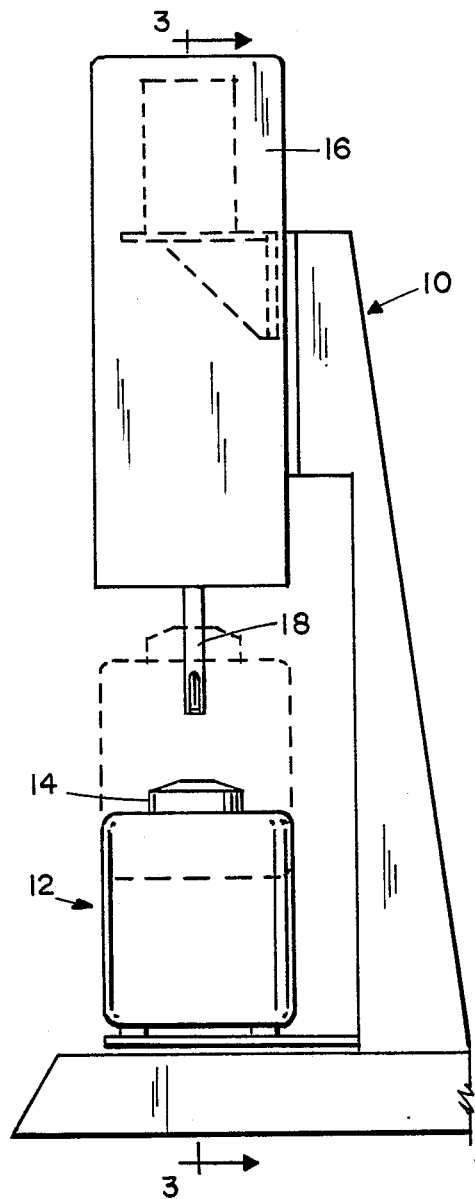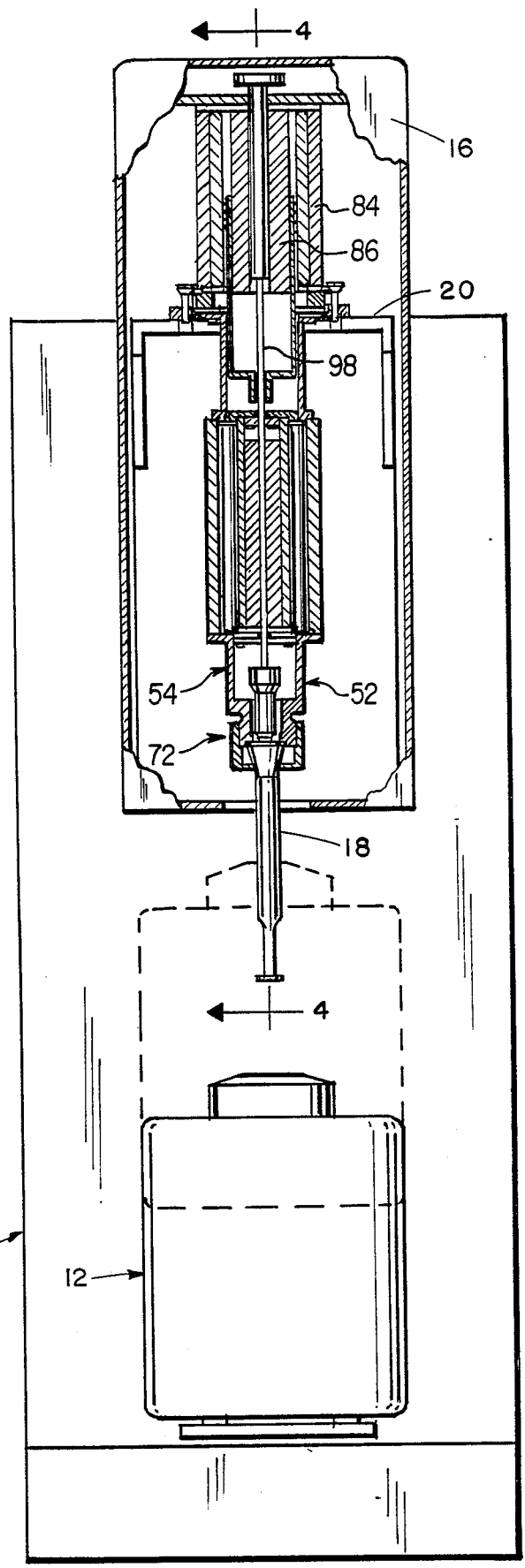
FIG. 2
FIG. 3

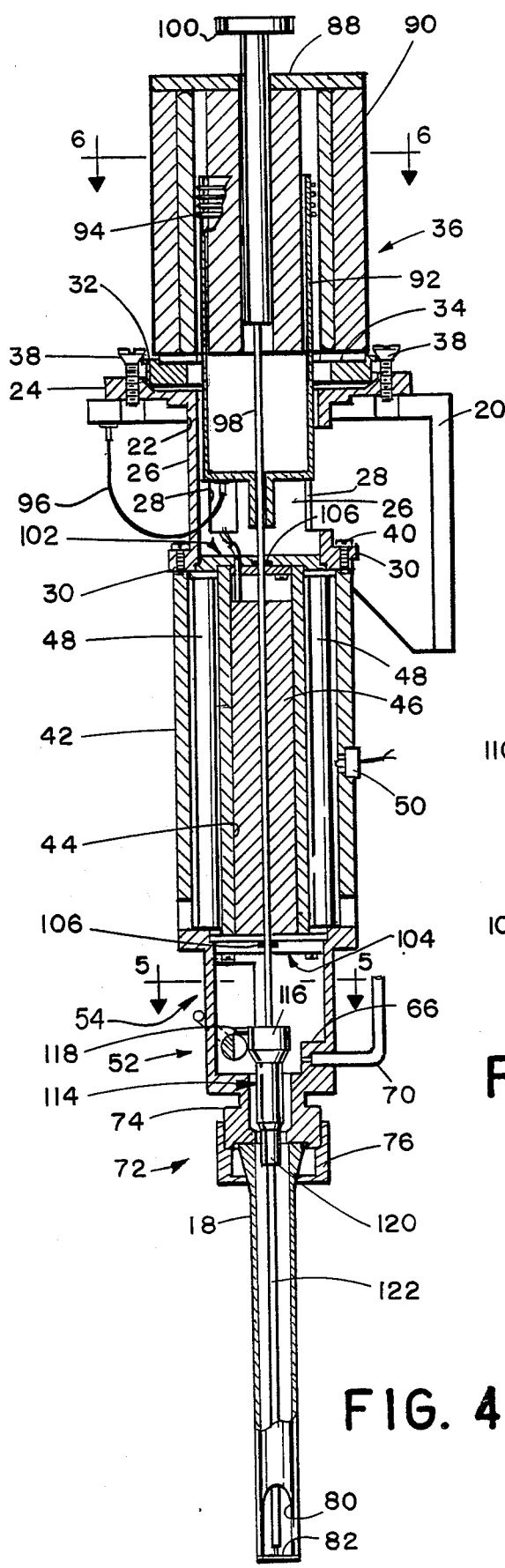
FIG. 4
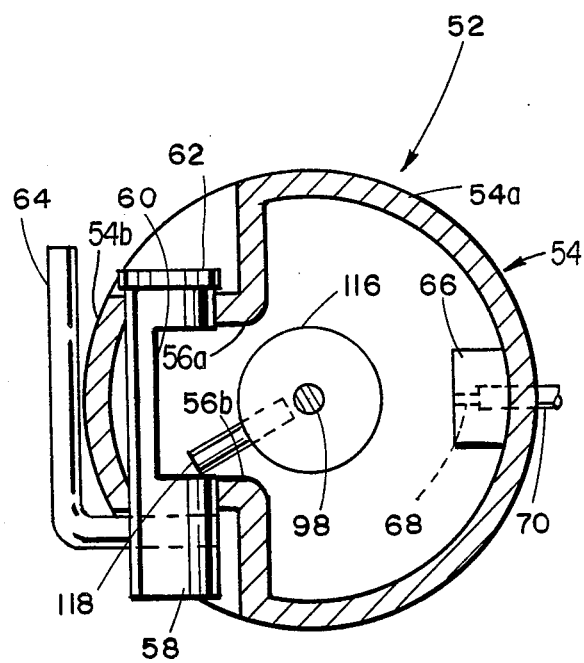
FIG. 5
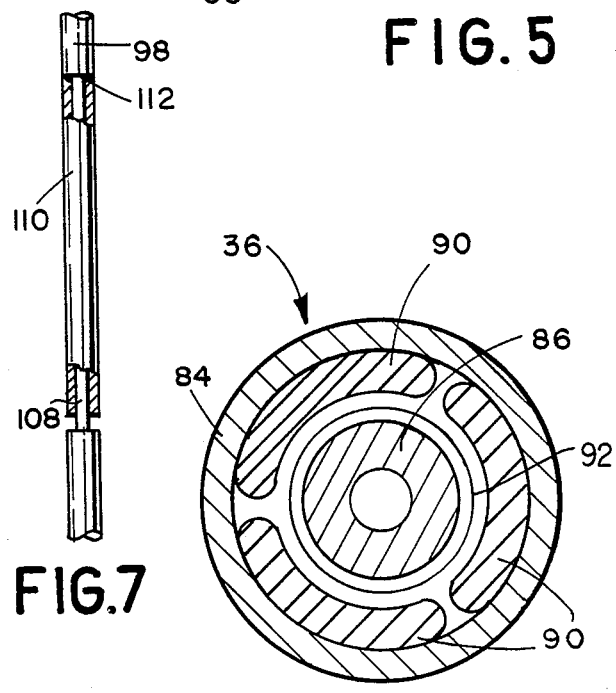
FIG. 6
FIG. 7

THERMOMECHANICAL ANALYSIS APPARATUS

TECHNICAL FIELD

The field of this invention is that of instruments designed to measure physical responses in samples undergoing temperature changes.

BACKGROUND ART

In U.S. Pat. No. 3,589,167, which issued June 29, 1971 to the assignee of the present invention, there is disclosed a thermomechanical analysis apparatus. That apparatus includes a probe assembly which is suspended in substantially weightless contact with a sample material over a range of displacement of the probe. This substantially weightless contact is achieved by means of a fluid reservoir and a float which is submerged in the fluid and coupled to the probe. Weights are added manually to the probe assembly to just offset the buoyancy of the float. As the height of a sample under test changes, the substantially weightless probe moves up or down in response.

Vertical movement of the probe assembly of the referenced prior art device is sensed by a conventional linear variable differential transformer (LVDT). The magnetic core of the LVDT is mounted on a non-magnetic rod which supports the probe. In this prior art device, a rack and pinion are provided for moving the LVDT coil assembly to achieve a null prior to beginning a measurement. The rod member which supports the probe passes through a pair of roller bearings. The entire assembly is suspended from a frame at a pair of spaced support points.

It is an object of the present invention to provide an apparatus which is simpler to use and more accurate than that of the prior art. Another object is to provide such an apparatus which eliminates the need for a fluid and a float. Another object is to provide such an apparatus wherein the use of weights during analysis is not required. Another object is to provide such an apparatus wherein mechanical adjustment of the LVDT for nulling purposes is avoided. Another object is to provide such an apparatus wherein friction is reduced by omitting bearings. Another object is to provide such an apparatus wherein potential friction and misalignment problems arising from a two point support are eliminated. The manner in which the foregoing objects are achieved will be more apparent from the following description and appended claims.

SUMMARY OF THE INVENTION

Briefly, in a thermomechanical analysis apparatus of the type which includes a support for positioning a sample in a programmable temperature environment, a vertical displaceable probe positionable in contact with the sample surface, means supporting the probe for substantially offsetting the effect of the weight of the probe on the sample, and means for monitoring movement of the probe in response to changing physical characteristics of the sample, the invention is directed to the improvement wherein the weight offsetting means is a linear motor. This linear motor comprises a substantially cylindrical magnet assembly mounted above and substantially coaxial with said probe. The linear motor also includes a linearly, vertically movable armature coaxial with the magnet assembly and including a coil energizable to generate a magnetic field operable with the field of said magnet assembly to exert a vertical axial force on the armature. Further, means are provided for controllably energizing the coil with an electrical current.

BRIEF DESCRIPTION OF DRAWINGS

FIG. 2 is an elevational view of apparatus constructed in accordance with the invention;

FIG. 3 is an enlarged longitudinal-section taken along the line 3—3 of FIG. 2;

FIG. 4 is an enlarged longitudinal-section taken substantially along the line 4—4 of FIG. 3;

FIG. 5 is an enlarged cross-section taken substantially along the line 5—5 of FIG. 4;

FIG. 6 is an enlarged cross-section taken substantially along the line 6—6 of FIG. 4; and FIG. 7 is a fragmentary elevational view, partially in axial section, illustrating the construction of the magnetic core of the linear variable differential transformer which forms part of the invention.

DESCRIPTION OF THE PREFERRED EMBODIMENT

Figure 1:
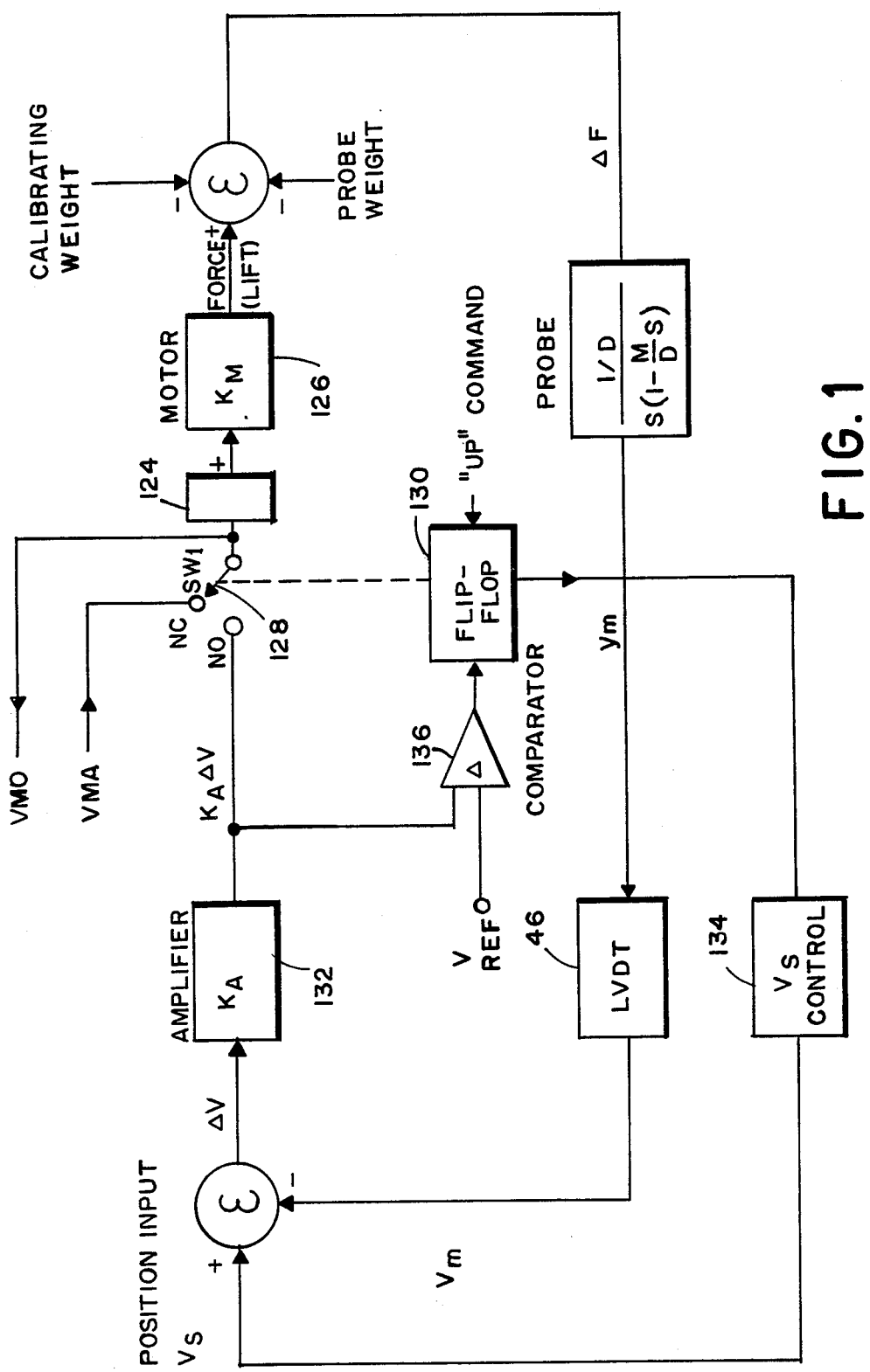
FIG. 1 is a block diagram of the electrical circuit for the apparatus of the invention.

With particular reference to FIG. 2, there is illustrated an apparatus in accordance with the invention comprising a stand 10 upon which is positioned a furnace and heat exchanger assembly 12. This assembly is similar to that of the above-referenced prior art patent: it includes an electrically heated furnace 14, and means by which the assembly may be cooled by liquid nitrogen. In this fashion the assembly 12 may be programmed through a range of temperatures from −180° C. to 1000° C.

Suspended above the furnace (1) heat-exchanger 12 is a housing 16 from which depends a quartz furnace tube 18. The assembly 12 may be raised to a position 12′ as illustrated by the dashed lines where it will receive the furnace tube 18. As this feature is similar to that of the referenced prior art patent it will not be disclosed in detail.

Mounted on the stand 10 is a bracket 20 as may be most clearly seen in FIG. 4. The bracket 20 includes a central opening 22 upon which is positioned a mounting ring 24 by means of screws (not shown). Extending downwardly from the mounting ring 24 through the opening 22 is a cylinder 26 which has a number of cutouts 28 in its side wall and carries three outwardly radially spaced mounting lugs 30 on its lower end. The upper surface of mounting ring 24 has an annular, tapered seat 32. The surface of the seat 32 is ideally a spherical segment but for practical purposes it may be conical. Supported upon the seat 32 is the outer lower edges of a bearing ring 34 rectangular in cross-section. Bearing ring 34 is mounted to the bottom of a cylindrical magnet assembly 36. Four adjusting screws 38, threaded into mounting ring 24, have tapered heads bearing against the upper edge of the bearing ring 34.

By means of screws 40 extending through lugs 30, a cylindrical aluminum housing 42 is secured to the lower end of and in coaxial alignment with cylinder 26. Housing 42 includes a central opening 44 within which is mounted a conventional linear variable differential transformer (LVDT) 46. Housing 42 contains a pair of elongate wells disposed with their respective longitudinal axes coplanar with and on diametrically opposite sides of the housing axis, each well containing a cartridge heater 48. Temperature control is maintained by a sensor 50 mounted in the side of the housing 42.

Formed at the bottom of housing 42 and coaxial therewith is a substantially cylindrical chamber 52. As shown in FIG. 5, the side wall 54 includes a major cylindrical segment 54a exceeding 180° in its circumferential extent, and a minor cylindrical segment 54b in diametrical opposition to the major segment. Intermediate the proximate ends of the major and minor segments 54a and 54b, side wall 54 is formed with and completed by a pair of parallel, chordally extending, planar wall segments 56a and 56b containing coaxially aligned bearing apertures in which are journaled the respective ends of a hollow cylindrical pintle or latch pin 58 having a cut-out 60. Latch pin 58 is retained in its journal at one end by an enlarged head 62 and at the other by an L-shaped actuating lever 64. Protruding inwardly from the cylindrical segment 54a is a boss 66 which contains a port 68 communicating with the end of a scavenging gas delivery tube 70.

Coaxially depending from chamber 52 is a chuck 72 comprising an externally threaded male stud 74 and an internally threaded female clamp 76. These members cooperate in the usual manner to secure the tapered upper end of quartz furnace tube 18. This tube is similar to that disclosed in the above-referenced prior art patent and includes at its lower end a pair of aligned openings 80 and a sample support surface 82.

Returning now to the upper end of the apparatus, the magnet assembly 36 comprises one element of a linear motor. It comprises an iron outer cylinder 84 and a coaxial iron inner cylinder 86 which are joined at their upper ends by a magnetically permeable plate 88. The space between outer cylinder 84 and inner cylinder 86 is occupied by three permanent ceramic magnets 90 polarized such that the cylinders 84, 86 represent opposite poles of the magnet assembly.

Disposed in the air gap 89 remaining between the permanent magnets 90 and the inner cylinder 86 is a cylindrical aluminum armature 92 which is axially displaceable within the air gap. The armature 92 carries a coil 94 comprising a few turns of wire around its upper end which are connected to external terminals by very thin leads 96. The lower end of the armature 92 is secured to a non-magnetic actuator rod 98. The upper end of rod 98 carries a small weight tray 100.

At either end of the housing 42 the rod 98 passes through a respective bearing assembly 102, 104, each of which carries a Teflon O-ring 106. The inner diameter of O-rings 106 are very slightly larger than the actuator rod 98 so that they are essentially frictionless when the rod 98 is exactly vertical.

A portion of the rod 98 which is within the LVDT 46 has a reduced diameter portion 108 as will be seen in FIG. 7. Mounted upon this portion is the tubular magnetic core 110 of the LVDT. The core 110 is secured to the rod 98 as by epoxy 112 at one end only. In this manner the core 110 and rod 98 are free to expand and contract in response to temperature changes and magnetostrictive effects without the creation of mutual stresses.

The lower end of rod 98 carries a probe support member 114. The member 114 includes an upper shoulder 116 which is of a size to just fit within the inner diameter of the stud 74. As best seen in FIG. 5, member 114 carried a pin 118 which extends between the walls parallel wall segments 56a, 56b of the chamber 52. The lower end of probe support member 114 is drilled and tapped to receive a threaded metal stud 120 which is secured to the end of each of the quartz probes 122 intended for use in the apparatus.

The linear motor control system is illustrated in FIG. 1. A voltage-controlled high impedance current source 124 supplies the linear motor 126. Control voltage is applied to the source 124 through a two position switch 128 having normally closed (NC) and normaly open (NO) contacts as illustrated. Switch 128 is controlled by a flip-flop 130.

When the user desires to insert a sample between the sample support surface 82 and the lower end of probe 122, a switch is closed to initiate an "up" command to raise the probe. This actuates the flip-flop 130 which moves the switch 128 to close its normally open contact. The force output of the motor 126 is added algebraically to the probe weight and a calibrating weight, the calibrating weight being positioned upon tray 100. The resulting force ($\Delta F$) is affected by the transfer function of the mechanical system labelled "probe". The transfer function is defined by the viscous friction coefficient D and the mass M. The 1/S term in the transfer function represents integration since there is no restoring force (or spring constant) in the system.

The position of the shaft $Y_m$ is sensed by the LVDT 46 which generates a voltage $V_m$. This voltage is compared with a set-point voltage $V_s$ and the error voltage $\Delta V$ is amplified by amplifier 132 and controls the linear motor, thus closing the loop. The force output of linear motor 126 becomes whatever is required to raise the probe 122 in response to the $V_s$ ramp generator 134. The input voltage VMO is sampled and stored in memory while the system is in this closed loop mode.

The position input voltage Vs continues to increase until it reaches a value corresponding to a probe displacement of approximately 3 cms, permitting the user to adjust or replace a sample. A "down" command is then given. $V_s$ starts to decrease and the probe descends. When the probe touches the sample the amplified error voltage $K_A\Delta V$ starts to decrease very rapidly. When this voltage equals a predetermined voltage corresponding to a load slightly less than the probe weight, as determined by comparator 136 the flip-flop 130 returns switch 128 to its normally closed position. The motor is then controlled by the VMA input signal which is equal to the VMO signal previously measured and stored. Thus, the probe comes to rest on the sample with negligible force and thereafter tracks any dimensional changes in the sample.

The apparatus of this invention includes a number of important features in addition to those previously decribed. For example, in order to provide more accurate measurements free from the effect of changes in mounting dimensions, the entire assembly is suspended from one point on the bracket 20. As will be seen from FIG. 4, the entire "analytical train" is supported on the tapered seat 32.

Friction on the shaft which could contribute errors to the force measurement is substantially eliminated by the use of the Teflon rings previously described. Any residual lateral forces caused by asymmetry in the magnet assembly 36 can be nulled by deliberately altering the angle between the magnet axis and the rod 98. This is done by rotation of the adjusting screws 38 to slightly alter the relationship between the bearing ring 34 and the tapered seat 32.

The force generated by the linear motor is proportional to the current in the coil 94 and to the magnetic field strength. By employing a high impedance constant current source for driving the coil 94 it is unnecessary to make corrections for any self-heating of the coil. The aluminum armature 92 upon which the coil is wound behaves as a shorted turn. This provides electro-magnetic damping when the system is in the closed loop levitation mode described previously.

The system compensates for the weight of the shaft by measuring the coil current required to lift the probe assembly. As previously explained, this is initiated by the user when introducing a new sample. When the probe is lowered, the instrument automatically weighs the probe assembly until it rests on the sample. At this point a restoring force equal to the measured probe weight is generated by the motor so that there is negligible force on the sample. The LVDT adjustment provided by the rack and pinion of the prior art device is avoided by a longer LVDT which may be operated away from its null-point. Normally, when an LVDT is so operated, its ouput is temperature dependent. However, this is avoided in the instrument of the invention by the temperature control provided by the cartridge heaters 48 and sensor 50.

In order to change a probe the furnace tube 18 is removed by unscrewing the clamp 76. When the furnace tube is removed the probe 122, which was formerly supported by the support surface 82, drops and the pin 118 comes to rest on the floor of the chamber 52, passing through the cutout 60 of the latch 58. The lever 64 is then raised so as to position the latch 58 over the pin 118, temporarily clamping it in place. The probe 122 is then unscrewed and a new probe connected. In order to avoid damage or strain to portions of the assembly as, for example, to the wire leads 96, any rotation caused by threading the probe into or out of place is avoided by the pin 118 which is prevented from rotating more than permitted by parallel wall segments 56a, 56b (FIG. 5).

It is believed that the many advantages of this invention will now be apparent to those skilled in the art. It will also be apparent that many variations and modifications may be made in this invention without departing from its spirit and scope. Accordingly, the foregoing description is to be construed as illustrative only, rather than limiting. This invention is limited only by the scope of the following claims.

What is claimed is:

1. In a thermomechanical analysis apparatus of the type which includes a support for positioning a sample in a programmable temperature environment, a probe mounted for vertical displacement without generation of mechanically counteractive restoring force positionable in contact with the sample surface, means supporting the probe for substantially offsetting the effect of the weight of the probe on the sample, and means for monitoring movement of the probe in response to changing physical characteristics of said sample, the improvement wherein said weight offsetting means is a linear motor comprising:

a substantially cylindrical magnet assembly mounted above and substantially coaxial with said probe and said monitoring means;

a linearly, vertically movable armature coaxial with said magnet assembly and including a coil energizable to generate a magnetic field operable with the field of said magnet assembly to exert a vertical axial force on said armature;

said armature being electrically conductive and forming a shorted secondary turn to said coil, and means for controllably energizing said coil with a high impedance electrical current.

2. In a thermomechanical analysis apparatus of the type which includes a support for positioning a sample in a programmable temperature environment, a probe mounted for vertical displacement without generation of mechanically counteractive restoring force positionable in contact with the sample surface menas supporting the probe for substantially offsetting the effect of the weight of the probe on the sample, and means for monitoring movement of the probe in response to changing physical characteristics of said sample, the improvement wherein said weight offsetting means is a linear motor comprising:

a substantially cylindrical magnet assembly mounted above and substantially coaxial with said probe and said monitoring means;

a linearly, vertically movable armature coaxial with said magnet assembly and including a coil energizable to generate a magnetic field operable with the field of said magnet assembly to exert a vertical axial force on said armature; and means for controllable energizing said coil with an electrical current, said coil energizing means being a circuit comprising:

a high impedance current source;

a probe position sensor and a set point control;

means responsive to the outputs of said position sensor and set point control to generate an error signal;

means external to said circuit supplying a control signal voltage;

switching means having a first position for energizing said coil in accordance with said error signal in a closed loop mode to lift said probe and a second position for energizing said coil in an open loop mode in response to said control signal;

means responsive to the value of said error signal while in the closed loop mode to store said error signal value; and means operative with said switch in said second position to energize said coil in response to said external signal voltage by an amount proportional to said stored error signal value.

3. The improvement of claim 2 wherein said probe position sensor is a linear variable differential transformer.

4. The improvement of claim 3 wherein said probe support means is a non-magnetic vertical rod depending from said armature and said linear variable differential transformer comprises:

a substantially cylindrical, hollow coil housing surrounding said vertical rod;

a magnetic coil within said coil housing; and means securing said core to said verticl rod for permitting expansion and contraction of each of said core and rod without inducing strain therebetween.

5. The improvement of claim 4 wherein said core comprises a tube surrounding said rod, expandable and contractible therealong, and secured to said rod at substantially one location along their lengths.

6. The improvement of claim 4 wherein said coil housing includes temperatures control means.

7. The improvement of claim 6 wherein said temperature control menas comprises an electrical heater.

8. In a thermomechanical analysis apparatus of the type which includes a support for positioning a sample in a programmable temperature environment, a probe mounted for vertical displacement without generation of mechanically counteractive restoring force positionable in contact with the sample surface, means supporting the probe for substantially offsetting the effect of the weight of the probe on the sample, and means for monitoring movement of the probe in response to changing physical characteristics of said sample, the improvement wherein said weight offsetting means is a linear motor comprising:

a substantially cylindrical magnet assembly mounted above and substantially coaxial with said probe and said monitoring means; said magnet assembly including mount means for adjusting the vertical alignment of the axis of said cylindrical magnet assembly; said mount means comprising:

a support member having a substantially circular, ring shaped, tapered seat symmetrical about a vertical axis;

a bearing ring carried by said magnet assembly and positionable on said seat; and clamping means for adjustably positioning and clamping said bearing ring relative to said seat;

a linearly, vertically movable armature coaxial with said magnet assembly and including a coil energizable to generate a magnetic field operable with the field of said magnet assembly to exert a vertical axial force on said armature; and means for controllably energizing said coil with an electrical current.

9. The improvement of claim 8 wherein said thermomechanical analysis apparatus is suspended substantially entirely from said support member.

* * * * *